(12) United States Patent
Millan Rodriguez et al.

(10) Patent No.: US 6,372,452 B1
(45) Date of Patent: Apr. 16, 2002

(54) PROCESS FOR OBTAINING PLANT PEPTONES WITH A HIGH HYDROLYSIS DEGREE AND APPLICATIONS THEREOF

(75) Inventors: Francisco Millan Rodriguez; Juan Bautista Palomas; Jose Manuel Olias Jimenez, all of Seville (ES)

(73) Assignees: Consejo Superior de Investigaciones Cientificas, Madrid; Universidad de Seville, Seville, both of (ES)

( * ) Notice: Subject to any disclaimer, the term of this patent is extended or adjusted under 35 U.S.C. 154(b) by 0 days.

(21) Appl. No.: 09/101,937
(22) PCT Filed: Nov. 28, 1997
(86) PCT No.: PCT/ES97/00294
§ 371 Date: Nov. 8, 1998
§ 102(e) Date: Nov. 8, 1998
(87) PCT Pub. No.: WO98/23170
PCT Pub. Date: Jun. 4, 1998

(30) Foreign Application Priority Data

Nov. 29, 1996 (ES) .............................................. 9602526

(51) Int. Cl.[7] ................................................ C12P 21/06
(52) U.S. Cl. ........................ 435/68.1; 435/272; 426/52
(58) Field of Search ............................... 435/68.1, 272; 426/52

(56) References Cited

FOREIGN PATENT DOCUMENTS

WO    WO 94/25580    * 11/1994

OTHER PUBLICATIONS

Parrado et al, J. Agric. Food Chem, 39:447–450, 1991.*

* cited by examiner

Primary Examiner—Francisco Prats
(74) Attorney, Agent, or Firm—Ladas & Parry

(57) ABSTRACT

The process includes a first stage to eliminate polyphenols from the starting vegetable isolates, followed by a double hydrolysis treatment, firstly with non-specific endoproteases and then, with specific endoproteases and exoproteases. The hydrolyzed peptones obtained in this way are applicable to the agroalimentary and medico-pharmaceutical industries, especially in the sectors of human, animal and clinical nutrition.

5 Claims, 1 Drawing Sheet

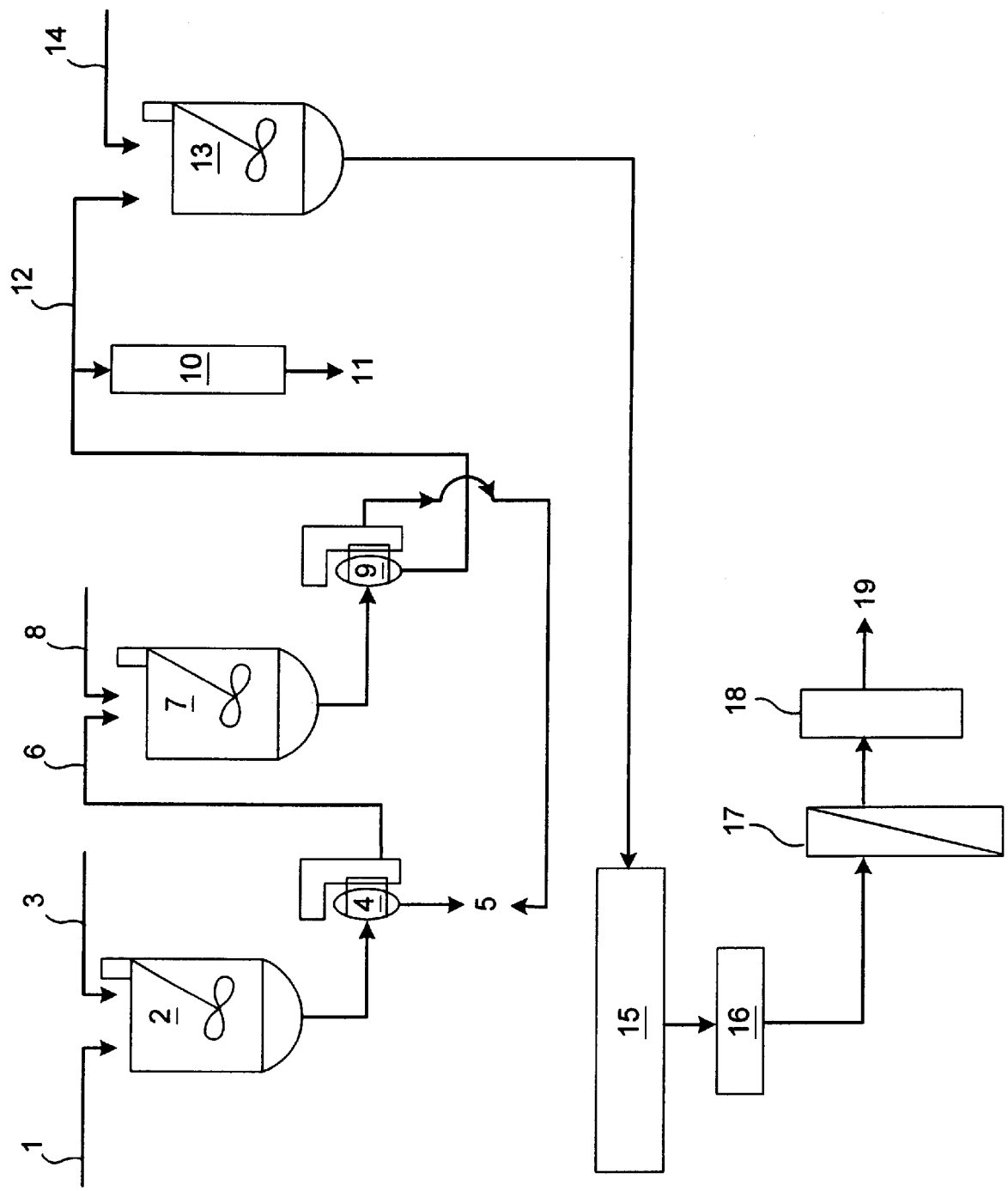

PROCESS FOR OBTAINING PLANT PEPTONES WITH A HIGH HYDROLYSIS DEGREE AND APPLICATIONS THEREOF

TECHNICAL FIELD OF THE INVENTION

This invention pertains to the technical field of the Agroalimentary and Medico-Pharmaceutical Industries and especially refers to human, animal and clinical nutrition.

More specifically, the invention provides a process to obtain vegetable peptones with a high degree of hydrolysis of great interest in the mentioned technical sectors.

STATE OF THE ART PRIOR TO THE INVENTION

The availability of different types of hydrolyzates in sufficiently large amounts and at reasonable prices would be of great importance and use for the preparation of special diets which, at present, are very expensive and hence, hardly used, although advisable from a medical standpoint.

Current societies and, particularly, those of developed countries, do not require random hydrolyzates [Parrado, J., Millán, F, Hernández-Pinzón, I., Bautista J and Machado A., 1993. Process Biochem., 28, 109–113; Ziajku S., Dzwolak W and Zubel J., 1994, Milk Science International, 49,7] aimed at general nutrition, culture of micro-organisms, additives for beverages, etc. Nowadays, hydrolyzates are required having well defined compositions and characteristics, either because they are not available on the market or because those existing are very expensive and need to be cheapened. Having hydrolyzates with a defined amino-acid composition [Parrado J., Millán F., Hernández-Pinzón., Bautista J and Machado A., 1993, J. Agr. Food Chem. 41, 1821–1825; Bautista J., Hernández-Pinzón I., Alaiz M., Parrado J and Millán F., 1996, J. Agr. Food Chem. 44, 967–971] is very desirable, both for the nutrition industry and the medico-pharmaceutical ones [Furst P., 1992, Clin. Nutr. 10, 519–529]. Hence, for example, branched aminoacid (AAR) enrichened hydrolyzates, either with mixtures of free aminoacids or with peptides rich in AAR, have been successfully used in the treatment of various hepatic pathologies, especially encephalopathies, Grunggreiff K., Kleine F. D., Musie H. E., Diete U., Franke D., Klanck S., Page I., Kleine S., Losene B and Pfeiffer K. P., 1993, Z-Gaskoenterol, 31, 235–241; Rossi-Fanelli F., 1990, Adv. Exp. Med. Biol. 272, 227–233].

The production of proteic hydrolyzates from residues rich in proteins (meat flour) and non-conventional protein sources (vegetable proteins) [Anuario de Estadistica Agraria 1996, Edited by the Technical Department of the Ministry of Agriculture, Fisheries and Food; Boatright W. L., Hettiarachchy N. S., 1995 JAOLS, 72, 1445–1451; Paredes-López O., Ordorica-Falomir C., Olivares-Vázquez M. R., 1991 J. Food Sci. 53, 1396–1398] is a well established process in the food industry.

Enzymatic hydrolysis is a very efficient process which, moreover, may be performed under reasonable conditions of temperature, pH and pressure, such that the nutritional quality of the amino-acids is maintained practically un-changed, since the destruction or modification of certain amino-acid residues does not take place, different to the case of chemical hydrolysis. In enzymatic hydrolysis, hydralyzate neutralization is avoided and hence, the high content in salts which would limit the use of hydrolyzates in certain applications, for example, in diet foods and parenteral preparations.

In recent years, many enzymatic protein hydrolysis processes have been studied for their application at a commercial scale. The interest for these types of process is large and, although the production of simple proteic hydrylyzates is not a problem, the production of defined hydrolyzates, namely, well defined ones, as demanded by the market, continues to be a problem and represents the greatest challenge in this field. The latter type of hydrolyzate, if possible, should combine the following characteristics: (I) perfectly defined composition in relation to the amino-acids contained (aminogram), as well as their size distribution (% in peptides, oligo-peptides, tetra-tri-dipeptides and free aminoacids); (ii) absence of or a negligible bitter flavour and, (iii) be hypoalergenic.

The patents existing to obtain proteic hydrolyzates, including both the chemical approach (use of acids and bases) and the enzymatic one (use of enzymes), are general and do not indicate the substrates used nor, in the case of enzymatic hydrolysis, the enzymes employed and of course, do not include the details (Patent 489358, No. 2278/79. Industrial Property Register. Nestlé).

DETAILED DESCRIPTION OF THE INVENTION

This invention, as indicated in the title, refers to a process to obtain vegetable peptones with a high degree of hydrolysis.

More specifically, in this report, the process to obtain enzymatic hydrolyzates of vegetable proteins with a high degree of hydrolysis (GH 50%) is described, specifying, the substrate(s) used [sunflowers, rape seeds, chickpeas, lentils, lupins and grape refuse] and the enzymes employed, including their commercial name. The process is the basis to obtain what has been called "customised hydrolyzates".

The main purpose is to include the preparation of the substrates, which in all cases implies the elimination of the polyphenols. The elimination of the latter, present in all vegetable protein isolates, is necessary because these substances generally inhibit the enzymatic activity of the proteases, such that their elimination is absolutely necessary for the efficient operation of the process.

The second important purpose is the optimization of the hydrolysis process whose treatment with more than one protease, is based on the resistance to hydrolysis of the allergic "epitopes" present in proteins. For this reason, in an initial treatment, the proteins are hydrolyzed with a) some endoprotease(s) with non-specific activity(ies), such that in a second step, once a practically constant degree of hydrolysis has been reached (12–15% depending on the substrate), a mixture of more specific endoproteases and exoproteases are added together (resulting in degrees of hydrolysis $\geq 50\%$), such that the probabilities of destroying the allergenic "epitopes" is almost total, besides eliminating the possible bitter flavor of some hydrolyzates. The proteolytic enzymes that have been used in each substrate are: ALKALASE™, KERASE™ and FLAVOURZYME™ for sunflower proteins; L-600 and FLAVOURZYME™ for rape seed; goglet and FLAVOURZYME™ for chickpeas, lentils and lupinus proteins; alkalase and kerase for grape refuse proteins. The hydrolyzates are concentrated and micronized to give a dry product.

Below, the characteristics and specifications of the aforementioned proteolytic enzymes used in this invention are indicated:

ALCALASE™ enzyme preparation: more specifically, ALCALASE™ 2.4 L, is a bacterial protease, being highly effective and specifically developed for the hydrolysis of all types of proteins. It is products at from a selected strain of Bacillus Licheniformes. It is an endopeptidase with an approximate molecular weight of 27,300 daltons. It is easily soluble in water at all concentrations and its density is 1.18 g/ml. It has an activity of 2.4 Anson Units per gram (Au/g), optimum pH of 8 and optimum temperature of 50° C.–60° C. It is available in the liquid form and is available from the company, Novo Nordisk Bioindustrial S.A.

FLAVOURZYME™ enzyme preparation: FLAVOURZYME™ more specifically, FLAVOURZYME™ 1,000 MG, is produced by the fermentation of Aspergillus oryzae and contains endoprotease and exopeptidase activity. The molecular weight differs from the different endoproteases, since it is an endo- and exo-protease complex. It is easily soluble in water, has an activity of 1,000 LAPU/g, optimum pH of 7 and optimum temperature of 50° C. It comes in its 35granulated form and is available from Novo Nordisk Bioindustrial S.A.

KERASE™ enzyme preparation: this is a microbial enzyme and is obtained from Streptomyces Fradiae. It is a mixture of endo- and exo-peptidase, which behave like serin protease and is stable in the presence of oxygen. It is non-toxic, free from antibiotics and bacterial contamination. It is easily soluble in water, has an activity of $10^{-8}$ Katal units/mg following the Anson method. It has an approximate molecular weight of 20,000 Daltons. The maximum activity pH is 8 and optimum temperature 55° C. It comes in the powder form and is produced by Compania Espanola de la Penicilina y Antibioticos, S.a. (CEPA, S.A.).

L-600™ enzyme preparation: This is a microbial protease serin. It is an endo-protease with an approximate molecular weight of 22,500 Daltons, optimum pH of 10 and optimum temperature of 60° C. It is easily soluble in water, has an activity of 66,000 DU/ml (Delf/ml). It comes in the liquid form and is available from the company MKC.

According to the above, the process of this invention allows the attainment, at a semi-preparation scale of proteic concentrates and isolates as from agroindustrial waste (sunflower, rape seed, grape refuse, lupin etc.) These proteic concentrates and isolates are the starting point to obtain different types of hydrolyzate, by the use of proteases. Moreover, it is possible to obtain the following at a practical level: hydrolyzates rich in branched amino-acids, glutamine, destined to clinical nutrition; hydrolyzates rich in sulphurated aminoacid destined to the nutrition of calves and suckling pigs, as well as hypoallergenic hydrolyzates destined to child nutrition.

BRIEF DESCRIPTION OF THE FIGURE

The only FIGURE attached to this description represents an illustrative scheme for a specific execution of the invention process. Said scheme includes each stage and the material flow which should be followed to achieve a correct preparation process.

THE NUMERICAL REFERENCES HAVE THE FOLLOWING MEANING:

1. Sunflower cake.
2. Protein extraction tank
3. Alkaline solution
4. Centrifuge
5. Soluble fraction
6. Soluble protein
7. Precipitation tank
8. Acid solution
9. Centrifuge
10. Atomizer
11. Dry isolate
12. Protein
13. Enzymatic reaction tank
14. Enzymatic solution
15. Hydrolyzate
16. Clarifier
17. Micro/ultrafiltration
18. Atomizer
19. Commercial hydrolyzate.

EMBODIMENTS OF THE INVENTION

This invention is additionally illustrated by the following example, which does not intend to limit its scope.

In said example, the process used to obtain an enzymatic hydrolyzate of sunflower vegetable protein, with degrees of hydrolysis $\geq 50\%$ is described in detail.

EXAMPLE

The fractionation of degreased sunflower flour (HG) is the first stage of the process. By means of a flotation/sedimentation tower system, separation of the lignocelullosic fraction (FLC), soluble fraction (FS) and proteic fraction (FP) is performed. The proteic fraction obtained in the previous stage, is subjected, within a treatment tank, to an elimination process of the phenols present by rinsing with water: ethanol (90:10). Once this stage is completed, solubilization of the protein is carried out. To perform the latter, the proteic fraction, free from polyphenols is extracted in an aerobic medium with an alkaline solution. This stage uses an extraction tank with upper stirring, circuit breaker, reagent addition system, pH and temperature control. Likewise, a clarifying centrifuge and decanters are used.

The proteic extract obtained in an aerobic alkakine medium, is centrifuged and precipitated at its isoelectric point in a treatment tank with upper stirring, acid addition system and pH control. With the process described until now, the preparation is obtained, of the proteic isolate to be used as a substrate for enzymatic hydrolysis.

The isolate, at suitable concentrations, is hydrolyzed with alkalase until 12% hydrolysis and then kerase and flavourzyme are added. The proteolytic enzymes used are endopeptidases and exopeptidases. The degree of hydrolysis (GH) is determined by the pH-stat method described by Adler-Nissen (1986, Elsevier App/. Scc. Publi.). The reactor used is of stainless steel, with systems for stirring, addition of water and reagents, as well as pH and temperature control.

Once finished the hydrolysis process, it is passed through a clarifying filter to eliminate solids in suspension and microemulsion. Then, it is fractionated by ultra-filtration to obtain customized peptides and finally, the material obtained is dried for its conservation.

| MATERIALS FOR THE TOTAL PROCESS | | | | |
|---|---|---|---|---|
| | Initial Weight | % Protein | Finished Kg | Y (%) |
| HG | 5,000 Kg | 25 | 1250 | 100 |
| FP | 1,500 Kg | 50 | 750 | 60 |
| Isolate | 650 Kg | 90 | 585 | 47 |
| Hydrolyzate | 468 Kg | 95 | 445 | 36 |

What is claimed is:

1. A process to obtain vegetable peptones with a degree of hydrolysis equal to or greater than 50%, said process comprising:
- (a) providing a vegetable protein;
- (b) subjecting the vegetable protein to a treatment that eliminates polyphenols so as to form from said vegetable protein a polyphenol free protein isolate;
- (c) subjecting the polyphenol free protein isolate to a first hydrolysis treatment with at least one endoprotease that hydrolyzes the protein isolate to form a first hydrolyzed product having a degree of hydrolysis of between about 12–15%;
- (d) subjecting the first hydrolyzed product to a second hydrolysis treatment with a mixture of an endoprotease and an exoprotease, which mixture hydrolyzes the first hydrolyzed product to form a second hydrolyzed product having a degree of hydrolysis equal to or greater than 50%; and
- (e) recovering the second hydrolyzed product.

2. A process according to claim 1, wherein the vegetable protein provided in step (a) is selected from the group consisting of sunflower, rape seed, chickpea, lentil, lupin, and a grape residue.

3. A process according to claim 1, wherein the recovery step (e) comprises the steps of concentrating and drying the second hydrolyzed product.

4. A process according to claim 1, wherein the endoprotease in step (c) or the mixture of the endoprotease and exoprotease in step (d) comprises a proteolytic enzyme selected from the group consisting of ALCALASE™, KERASE™, FLAVOURZYME™ and L-600.

5. A process according to claim 1, comprising incorporating the second hydrolyzed product recovered in step (e) into a nutritional product.

* * * * *